(12) United States Patent
Li et al.

(10) Patent No.: US 6,670,125 B2
(45) Date of Patent: Dec. 30, 2003

(54) METHODS FOR DETECTING FOR THE PRESENCE OF TUMOR CELLS AND FOR SCREENING FOR ANTI-TUMOR AGENTS

(75) Inventors: Xuri Li, Stockholm (SE); Karin Aase, Stockholm (SE); Ulf Eriksson, Stockholm (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/858,891

(22) Filed: May 17, 2001

(65) Prior Publication Data

US 2002/0081637 A1 Jun. 27, 2002

Related U.S. Application Data

(60) Provisional application No. 60/204,748, filed on May 17, 2000.

(51) Int. Cl.$^7$ .................. C12Q 1/68; G01N 33/574; G01N 33/53

(52) U.S. Cl. .................. 435/6; 435/7.23; 435/7.1; 435/7.21

(58) Field of Search .................. 435/4, 7.1, 6, 7.21, 435/7.23

(56) References Cited

PUBLICATIONS

Salven, et al., 1998, Am. J. Pathology, 153(1):103–8.*
Sowter, et al., 1997 Lab Investigation, 77(6):607–14.*

* cited by examiner

Primary Examiner—Mary E. Mosher
Assistant Examiner—Misook Yu
(74) Attorney, Agent, or Firm—Crowell & Moring LLP

(57) ABSTRACT

A method and kit for detecting the presence of tumor cells in an animal by detecting expression of VEGF-$B_{186}$, determining an increased expression of VEGF-$B_{186}$, or by determining an increased expression of VEGF-$B_{186}$ relative to expression of VEGF-$B_{167}$. The kit comprises a receptacle adapted to receive a sample and a means for detecting expression of VEGF-$B_{186}$ from the sample. Also, a method for screening for anti-tumor agents.

21 Claims, 6 Drawing Sheets

| Tissues | VEGF-B 167 | VEGF-B 186 | VEGF-B186 / VEGF-B167 (%) |
|---|---|---|---|
| heart | 27 | 7.3 | 27 |
| skeletal muscle | 27 | 3.2 | 12 |
| diaphragm | 16 | 3 | 19 |
| colon | 7 | 1.7 | 24 |
| cerebellum | 6 | - | - |
| eye | 6 | - | - |
| kidney | 4 | 1 | 25 |
| brain | 4 | 0.6 | 15 |
| adrenal | 4 | - | - |
| lung | 3 | 0.45 | 15 |
| cerebrum | 3 | - | - |
| liver | 1 | - | - |
| testis | 0.5 | - | - |
| small intestine | 0.5 | - | - |
| spleen | 0.5 | - | - |
| thymus | 0.5 | - | - |
| peripheral blood cells | 0.2 | - | - |
| T241 | 12 | 7.4 | 62 |
| B16 | 9 | 4.5 | 50 |
| BT4C | 8 | 6.3 | 79 |
| LLC | 6 | 3.2 | 53 |

Figure 3

SEQUENCE LISTING

<160> NUMBER OF SEQ ID NOS: 4

<210> SEQ ID NO 1
<211> LENGTH: 25

-continued

```
<212> TYPE: DNA
<213> ORGANISM: Murinae gen. sp.

<400> SEQUENCE: 1
acgtagatct agccccagga tcctc                                          25

<210> SEQ ID NO 2
<211> LENGTH: 28
<212> TYPE: DNA
<213> ORGANISM: Murinae gen. sp.

<400> SEQUENCE: 2
acgtgaattc tcagccccgc ccttggca                                       28

<210> SEQ ID NO 3
<211> LENGTH: 25
<212> TYPE: DNA
<213> ORGANISM: Murinae gen. sp.

<400> SEQUENCE: 3
acgtagatct agggttgcca taccc                                          25

<210> SEQ ID NO 4
<211> LENGTH: 29
<212> TYPE: DNA
<213> ORGANISM: Murinae gen. sp.

<400> SEQUENCE: 4
acgtgaattc tcagttgacg gcgctgggt                                      29
```

METHODS FOR DETECTING FOR THE PRESENCE OF TUMOR CELLS AND FOR SCREENING FOR ANTI-TUMOR AGENTS

This application claims the priority of U.S. provisional application Serial No. 60/204,748 filed May 17, 2000 in the name of Xuri LI et al.

BACKGROUND OF THE INVENTION

The following is only offered as background information to aid the reader in understanding the invention and is not admitted to be or describe prior art to the present invention.

The two major components of the mammalian vascular system are the endothelial and smooth muscle cells. The endothelial cells form the lining of the inner surface of all blood vessels and lymphatic vessels in the mammal. The formation of new blood vessels can occur by two different processes, vasculogenesis or angiogenesis (for review see Risau, W., Nature 386:671–674 (1997)). Vasculogenesis is characterized by the in situ differentiation of endothelial cell precursors to mature endothelial cells and association of these cells to form vessels, such as occurs in the formation of the primary vascular plexus in the early embryo. In contrast, angiogenesis, the formation of blood vessels by growth and branching of pre-existing vessels, is important in later embryogenesis and is responsible for the blood vessel growth which occurs in the adult. Angiogenesis is a physiologically complex process involving proliferation of endothelial cells, degradation of extracellular matrix, branching of vessels and subsequent cell adhesion events. In the adult, angiogenesis is tightly controlled and limited under normal circumstances to the female reproductive system. However angiogenesis can be switched on in response to tissue damage. Also solid tumors are able to induce angiogenesis in surrounding tissue, thus sustaining tumor growth and facilitating the formation of metastases (Folkman, J., Nature Med. 1:27–31, (1995)). The molecular mechanisms underlying the complex angiogenic processes are far from being understood.

Angiogenesis is also involved in a number of pathologic conditions, where it plays a role or is involved directly in different sequelae of the disease. Some examples include neovascularization associated with various liver diseases, neovascular sequelae of diabetes, neovascular sequelae to hypertension, neovascularization in post-trauma, neovascularization due to head trauma, neovascularization in chronic liver infection (e.g. chronic hepatitis), neovascularization due to heat or cold trauma, dysfunction related to excess of hormone, and creation of hemangiomas and restenosis following angioplasty. In arthritis, new capillaries invade the joint and destroy cartilage. In diabetes, new capillaries in the retina invade the vitreous humour, causing bleeding and blindness (Folkman, J. and Shing, Y., J. Biol. Chem. 267:10931–10934 (1992)). The role of angiogenic factors in these and other diseases has not yet been clearly established.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See Folkman et al, J. Biol. Chem., 267:10931–10934 (1992) for a review.

It has been suggested that a particular family of endothelial cell-specific growth factors, the vascular endothelial growth factors (VEGFs), and their corresponding receptors are primarily responsible for stimulation of endothelial cell growth and differentiation, and for certain functions of the differentiated cells. These factors are members of the PDGF/VEGF family, and appear to act primarily via endothelial receptor tyrosine kinases (RTKs). The PDGF/VEGF family of growth factors belongs to the cystine-knot superfamily of growth factors, which also includes the neurotrophins and transforming growth factor-β.

Eight different proteins have been identified in the PDGF/VEGF family, namely two PDGFs (A and B), VEGF and five members that are closely related to VEGF. The five members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C or VEGF2, described in Joukov et al, EMBO J. 15:290–298 (1996), Lee et al, Proc. Natl. Acad. Sci. USA 93:1988–1992 (1996), and U.S. Pat. Nos. 5,932, 540 and 5,935,540 by Human Genome Sciences, Inc; VEGF-D, described in International Patent Application No. PCT/US97/14696 (WO 98/07832), and Achen et al, Proc. Natl. Acad. Sci. USA 95:548–553 (1998); the placenta growth factor (PlGF), described in Maglione et al, Proc. Natl. Acad. Sci. USA 88:9267–9271 (1991); and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the eight conserved cysteine residues which form the cystine-knot motif. In their active, physiological state, the proteins are dimers formed by disulfide bonding, by both inter- and intramolecular bonds, at the eight cysteine residues. Functional characteristics of the VEGF family include varying degrees of mitogenicity for endothelial cells and related cell types, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., Nature, 380: 435–439, (1996); Ferrara et al., Nature, 380: 439–442, (1996); reviewed in Ferrara and Davis-Smyth, Endocrine Rev., 18: 4–25, (1997)). The significance of the role played by VEGF has been demonstrated in studies showing that inactivation of a single VEGF allele results in embryonic lethality due to failed development of the vasculature (Carmeliet et al., Nature, 380: 435–439, (1996); Ferrara et al., Nature, 380: 439–442, (1996)). The isolation and properties of VEGF have been reviewed; see Ferrara et al., J. Cellular Biochem., 47: 211–218, (1991) and Connolly, J. Cellular Biochem., 47: 219–223, (1991).

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF is also chemotactic for certain hematopoetic cells. Recent literature indicates that VEGF blocks maturation of dendritic cells and thereby reduces the effectiveness of the immune response to tumors (many tumors secrete VEGF) (Gabrilovich et al., Blood 92: 4150–4166, (1998); Gabrilovich et al., Clinical Cancer Research 5: 2963–2970, (1999)).

Vascular endothelial growth factor B (VEGF-B) is a non-glycosylated, highly basic growth factor. VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF (Olofsson, B. et al, Proc. Natl. Acad. Sci. USA 93:2576–2581 (1996)). RT-PCR assays have demonstrated the presence of VEGF-B mRNA in melanoma, normal skin, and muscle. This suggests that VEGF and VEGF-B, despite the fact that they are co-expressed in many tissues, may have functional differences. Gene targeting studies have shown that VEGF-B deficiency results in mild cardiac phenotype, and impaired coronary vasculature (Bellomo et al, Circ. Res. 86:E29–35 (2000)).

Human VEGF-B was isolated using a yeast co-hybrid interaction trap screening technique by screening for cellular proteins which might interact with cellular retinoic acid-binding protein type I (CRABP-I). The isolation and characteristics including nucleotide and amino acid sequences for both the human and mouse VEGF-B are described in detail in PCT/US96/02957, in U.S. Pat. Nos. 5,840,693 and 5,607,918 by Ludwig Institute for Cancer Research and The University of Helsinki and in Olofsson et al, Proc. Natl. Acad. Sci. USA 93:2576–2581 (1996). The entire disclosures of International Patent Application PCT/US97/14696 (WO 98/07832), U.S. Pat. No. 5,840,693 and U.S. Pat. No. 5,607,918 are incorporated herein by reference.

The mouse and human genes for VEGF-B are almost identical, and both span about 4 kb of DNA. The genes are composed of seven exons and their exon-intron organization resembles that of the VEGF and PlGF genes (Grimmond et al, Genome Res. 6:124–131 (1996); Olofsson et al, J. Biol. Chem. 271:19310–19317 (1996); Townson et al, Biochem. Biophys. Res. Commun. 220:922-928 (1996)).

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 15: 290–298, (1996).

VEGF-D was isolated from a human breast cDNA library, commercially available from Clontech, by screening with an expressed sequence tag obtained from a human cDNA library designated "Soares Breast 3NbHBst" as a hybridization probe (Achen et al, Proc. Natl. Acad. Sci. USA, 95: 548–553, (1998)). Its isolation and characteristics are described in detail in International Patent Application No. PCT/US97/14696 (WO98/07832). In PCT/US97/14696, the isolation of a biologically active fragment of VEGF-D is also described. This fragment consists of VEGF-D amino acid residues 93 to 201.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 88: 9267–9271, (1991). Presently its biological function is not well understood.

VEGF3 was isolated from a cDNA library derived from colon tissue. VEGF3 is believed to have about 36% identity and about 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

As noted above, the PDGF/VEGF family members act primarily by binding to receptor tyrosine kinases. In general, receptor tyrosine kinases are glycoproteins, which consist of an extracellular domain capable of binding a specific growth factor(s), a transmembrane domain, which is usually an alpha-helical portion of the protein, a juxtamembrane domain, which is where the receptor may be regulated by, e.g., protein phosphorylation, a tyrosine kinase domain, which is the enzymatic component of the receptor and a carboxy-terminal tail, which in many receptors is involved in recognition and binding of the substrates for the tyrosine kinase.

Five endothelial cell-specific receptor tyrosine kinases have been identified, belonging to two distinct subclasses: three vascular endothelial cell growth factor receptors, VEGFR-1 (Flt-1), VEGFR-2 (KDR/Flk-1), VEGFR-3 (Flt4), and the two receptors of the Tie family, Tie and Tie-2 (Tek). These receptors differ in their specificity and affinity. All of these have the intrinsic tyrosine kinase activity which is necessary for signal transduction.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds PlGF. VEGF-B binds to VEGFR-1 with high affinity, but not to VEGFR-2 or -3 (Olofsson et al, Proc. Natl. Acad. Sci. USA, 95:11709–11714 (1998)). VEGF-C has been shown to be the ligand for VEGFR-3, and it also activates VEGFR-2 (Joukov et al, The EMBO Journal 15:290–298 (1996)). VEGF-D binds to both VEGFR-2 and VEGFR-3 (Achen et al, Proc. Natl. Acad. Sci. USA 95:548–553 (1998)). A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al, Cell 92:735-745 (1998)). The VEGF receptor was found to specifically bind the $VEGF_{165}$ isoform via the exon 7 encoded sequence, which shows weak affinity for heparin (Soker et al, Cell 92:735-745 (1998)). Surprisingly, the receptor was shown to be identical to human neuropilin-1 (NP-1), a receptor involved in early stage neuromorphogenesis. PlGF-2 also appears to interact with NP-1 (Migdal et al, J. Biol. Chem. 273:22272–22278 (1998)).

VEGFR-1, VEGFR-2 and VEGFR-3 are expressed differently by endothelial cells. Generally, both VEGFR-1 and VEGFR-2 are expressed in blood vessel endothelia (Oelrichs et al, Oncogene 8:11–18 (1992); Kaipainen et al, J. Exp. Med. 178:2077–2088 (1993); Dumont et al, Dev. Dyn. 203:80–92 (1995); Fong et al, Dev. Dyn. 207:1–10 (1996)) and VEGFR-3 is mostly expressed in the lymphatic endothelium of adult tissues (Kaipainen et al, Proc. Natl. Acad. Sci. USA 9:3566–3570 (1995)). VEGFR-3 is also expressed in the blood vasculature surrounding tumors.

Although VEGFR-1 is mainly expressed in endothelial cells during development, it can also be found in hematopoetic precursor cells during early stages of embryogenesis (Fong et al, Nature 376:66–70 (1995)). In adults, monocytes and macrophages also express this receptor (Barleon et al, Blood 87:3336–3343 (1995)). In embryos, VEGFR-1 is expressed by most, if not all, vessels (Breier et al, Dev. Dyn. 204:228–239 (1995); Fong et al, Dev. Dyn. 207:1–10 (1996)).

Since the identification and characterization of VEGF, a number of important findings have focused attention on the activity of angiogenic factors and the elucidation of new factors. The early findings showed that angiogenesis is required for normal development and physiology. Processes such as embryogenesis, wound healing, and corpus luteum formation, all involve angiogenesis and angiogenic factors. During wound healing, for example, VEGF mRNA levels increase suggesting a direct correlation between the expression of VEGF and the healing process. Also, a defect in VEGF regulation might be associated with wound healing disorders (Frank, S., et al, J. Biol. Chem. 2705:12607–12613 (1995)).

Another important finding involves the connection between angiogenesis and tumor development. Both tumor growth and metastasis are angiogenesis-dependent processes (Folkman, J. and Shing, Y., J. Biol. Chem. 267: 10931–10934 (1992)). For example, when tumor cells are introduced into an animal, the expression pattern of VEGF mRNA reveals expression at the highest level in cells at the periphery of necrotic, tumor growth areas. Numerous blood vessels were identified within these areas. The expression of VEGF in these areas suggests that hypoxemia, a state of deficient oxygenation, triggers expression and release of VEGF in the necrotic tumor. The expression of VEGF-B also has been directly correlated with tumor growth (see U.S. Pat. No. 5,840,693). VEGF-B expression is especially up regulated in tumor-associated macrophages and also in ovarian epithelial tumors (Sowter et al, Lab Invest. 77:607–14, (1997)). VEGF-B mRNA can be detected in most tumor cell lines investigated, including adenocarcinoma, breast carcinoma, lymphoma, squamous cell carcinoma, melanoma, fibrosarcoma and Schwannoma (Salven et al, Am J Pathol. 153:103–8 (1998)).

It has been shown that members of the VEGF/PDGF family produce variant transcripts. VEGF has been shown to display different transcripts because of alternative splicing. The human VEGF gene has five different mRNA species (Neufeld et al, FASEB J. 13:9–22 (1999)), resulting in proteins differing in their molecular mass and biological properties (Carmeliet, P., Nat. Med. 6:389–395 (2000)). The VEGF-$A_{165}$ isoform is the predominant transcript in most tissues, giving rise to a polypeptide with unique affinity to the neuropilin-1 receptor, besides the binding to VEGFR1 and VEGFR2. $VEGF_{121}$, and $VEGF_{189}$ are expressed in normal tissues at lower levels. Isoform specific VEGF targeting experiment has shown that $VEGF_{164}$ and $VEGF_{188}$ are more important for postnatal growth and maintenance of normal function of cardiovascular system, while $VEGF_{120}$, initiates and promotes vasculogenesis (Carmeliet et al, Nat Med. 5:495–502 (1999)). $VEGF_{206}$ is mainly expressed in embryonic tissues (Houck et al, Mol Endocrinol. 5:1806–14 (1991)), while $VEGF_{145}$ can only be found in tumor cell lines (Poltorak et al, J Biol Chem. 272:7151–8 (1997)). Moreover, VEGF is also regulated in an isoform-specific way under pathological conditions. In lung and colon carcinomas, $VEGF_{165}$ and $VEGF_{121}$ are up-regulated, whereas $VEGF_{189}$ is not changed, suggesting an isoform-specific role of VEGF in malignancy (Cheung et al, Hum Pathol. 29:910–4 (1998)).

The placenta growth factor (PLGF) has three different isoforms, which are expressed in a tissue and development specific way (Maglione et al, Oncogene 8:925–31 (1993); Cao et al, Biochem Biophys Res Commun. 235:493–8 (1997)).

Presently, two isoforms of VEGF-B, generated by alternative splicing of mRNA, have been recognized (Grimmond et al, Genome Res. 6:124–131 (1996); Olofsson et al, J. Biol. Chem. 271:19310–19317 (1996); Townson et al, Biochem. Biophys. Res. Commun. 220:922–928 (1996)). They are a cell associated form of 167 amino acid residues (VEGF-$B_{167}$) and a secreted form of 186 amino acid residues (VEGF-$B_{186}$). The isoforms have an identical N-terminal domain of 115 amino acid residues, excluding the signal sequence, while the C-terminal domains differ. The common N-terminal domain is encoded by exons 1–5. Differential use of the remaining three exons gives rise to the two splice isoforms. By the use of an alternative splice-acceptor site in exon 6, an insertion of 101 bp introduces a frame-shift and a stop of the coding region of VEGF-$B_{167}$ cDNA. Thus, the two VEGF-B isoforms have differing C-terminal domains.

The different C-terminal domains of the two splice isoforms of VEGF-B affect their biochemical and cell biological properties. The C-terminal domain of VEGF-$B_{167}$ is structurally related to the corresponding region in VEGF, with several conserved cysteine residues and stretches of basic amino acid residues. Thus, this domain is highly hydrophilic and basic and, accordingly, VEGF-$B_{167}$ will remain cell-associated on secretion, unless the producing cells are treated with heparin or high salt concentrations. The cell-associated molecules binding VEGF-$B_{167}$ are likely to be cell surface or pericellular heparin sulfate proteoglycans. It is likely that the cell-association of this isoform occurs via its unique basic C-terminal region.

The C-terminal domain of VEGF-$B_{186}$ has no significant similarity with known amino acid sequences in the databases. The hydrophobic character of the C-terminal domain of VEGF-$B_{186}$ contrasts with the properties of the hydrophilic and basic C-terminal domain of VEGF-$B_{167}$ This is supported by the observation that VEGF-$B_{186}$ does not remain cell-associated on its secretion. Recent evidence indicates that this isoform is proteolytically processed, which regulates the biological properties of the protein (Olofsson et al, Proc. Natl. Acad. Sci. USA, 95:11709–11714 (1998)).

The isolation of the human and mouse VEGF-B isoforms are described in detail in PCT/US96/02957, in U.S. Pat. Nos. 5,840,693 and 5,607,918 by Ludwig Institute for Cancer Research and The University of Helsinki and in Olofsson et al, Proc. Natl. Acad. Sci. USA 93:2576–2581 (1996).

Both isoforms of VEGF-B also form heterodimers with VEGF, consistent with the conservation of the eight cysteine residues involved in intermolecular and intramolecular disulfide bonding of PDGF-like proteins. Furthermore, co-expression of VEGF-B and VEGF in many tissues suggests that VEGF-B-VEGF heterodimers occur naturally. Heterodimers of VEGF-$B_{167}$-VEGF remain cell-associated. In contrast, heterodimers of VEGF-$B_{186}$ and VEGF are freely secreted from cells in a culture medium. VEGF also forms heterodimers with PLGF (DiSalvo, et al, J. Biol. Chem. 270:7717–7723 (1995)). The production of heterodimeric complexes between the members of this family of growth factors could provide a basis for a diverse array of angiogenic or regulatory molecules.

In previous studies regarding VEGF-B expression regulation, the two isoforms have not been separately investigated. In those cases where they were studied separately by RT-PCR, they do not accurately reflect the transcription levels. Previous data have shown high-level expressions of VEGF-B in different tumors and cell lines (Sowter et al, Lab Invest. 77:607–14, (1997); Salven et al, Am J Pathol. 153:103–8 (1998); and Enholm et al, Oncogene 14:2475–83 (1997)). However, most studies were based on immunohistochemistry, which can not distinguish the two isoforms. Thus the expression pattern and regulation of VEGF-$B_{167}$ and VEGF-$B_{186}$ remains obscure. A study of the expression pattern and regulation of VEGF-$B_{167}$ and VEGF-$B_{186}$ would be of particular importance to the further understanding of the role played by VEGF-B in both physiological and pathological conditions.

All references heretofore mentioned are incorporated by reference in the present application.

SUMMARY OF THE INVENTION

This invention relates to a method and kit for detecting potential the presence of tumor cells in an animal by detecting expression of VEGF-$B_{186}$ or by determining the increased expression of VEGF-$B_{186}$.

In one of its aspects, the invention provides a method of detecting a presence of tumor cells in an animal suspected of having a tumor. The method comprises obtaining a sample from the animal; and detecting expression of VEGF-$B_{186}$ from said sample, whereby detection of expression of VEGF-$B_{186}$ is indicative of the presence of tumor cells.

Alternatively, the method comprises obtaining a sample from the animal; determining the expression level of VEGF-$B_{186}$ from said sample; and comparing the expression level from the sample to an expression level of VEGF-$B_{186}$ normally expressed by this particular sample, whereby determination of an increased expression of VEGF-$B_{186}$ over the normal expression is indicative of the presence of tumor cells.

The sample can be a plasma, serum or tissue sample.

VEGF-$B_{186}$ can be detected using immunoassays, for example, radio or enzyme-linked and using a monoclonal antibody to VEGF-$B_{186}$ labeled with a detectable label. These assay can include use of soluble or immobilized VEGFR-1 and/or specific antibodies. The antibody may be coupled to a suitable supermagnetic, paramagnetic, electron dense, ecogenic or radioactive or non-radioactive agent for imaging. Examples of radioactive agents/labels include a radioactive atom or group, such as $^{125}$I or $^{32}$P. Examples of non-radioactive agents/labels include enzymatic labels, such as horseradish peroxidase or fluorimetric labels, such as fluorescein-5-isothiocyanate (FITC). Labeling may be direct or indirect, covalent or non-covalent.

The expression level of VEGF-$B_{186}$ can be determined by such methods as RNASE protection analysis.

It is contemplated that the comparison of expression level from the sample with the expression level of VEGF-$B_{186}$ normally expressed by a particular sample means that the sample having normal expression is of the same type sample, e.g. lung tissue, and of the same species, e.g. human, as that obtained from the animal suspected of having a tumor.

In another aspect, the invention provides a kit for detecting the presence of tumor cells in an animal. The kit comprises a receptacle adapted to receive a sample; and a means for detecting expression of VEGF-$B_{186}$ from the sample, whereby detection of VEGF-$B_{186}$ expression is indicative of tumor growth.

Alternatively the kit comprises a receptacle adapted to receive a sample; a means for determining an expression level of VEGF-$B_{186}$ from the sample; and a means for determining the normal expression level of VEGF-$B_{186}$ from this particular sample, whereby determination of an increased expression of VEGF-$B_{186}$ over the normal expression is indicative of tumor growth.

The detection means preferably is a monoclonal antibody to VEGF-$B_{186}$ labeled with a detectable label as described above.

It is contemplated that phase "the normal expression level of VEGF-$B_{186}$ from this particular sample" means that the expression level is or was determined from a sample of the same type sample, e.g. lung tissue, and of the same species, e.g. human, as that obtained from the animal suspected of having a tumor but without tumor growth in the particular sample.

The determining means can be any method such as RNASE protection analysis which can be used to determine the expression level of a particular polypeptide or it can be a chart or a list which provides the normal expression level of VEGF-$B_{186}$ from this "particular sample" as defined above.

In a further aspect, the invention provides a method for screening for anti-tumor agents. This method comprises applying a test agent to a tumor cell; and detecting, by any suitable means, a decrease in expression of VEGF-$B_{186}$ in the tumor cell.

BRIEF DESCRIPTION OF THE DRAWINGS

The invention will be described in further detail hereinafter with reference to the accompanying drawings in which:

FIG. 3 provides a table listing the determined expression levels of mouse VEGF-$B_{167}$ and of mouse VEGF-$B_{186}$ from various tissues using 30 pg and 100 pg of total cellular RNA, respectively, as well as the ratio of VEGF-$B_{186}$ expression level to VEGF-$B_{167}$ expression level for the various tissues;

DETAILED DESCRIPTION OF PREFERRED EMBODIMENTS

EXAMPLE 1

VEGF-$B_{167}$ is the Major Isoform Expressed in Both Adults and Embryos

Figure 1:
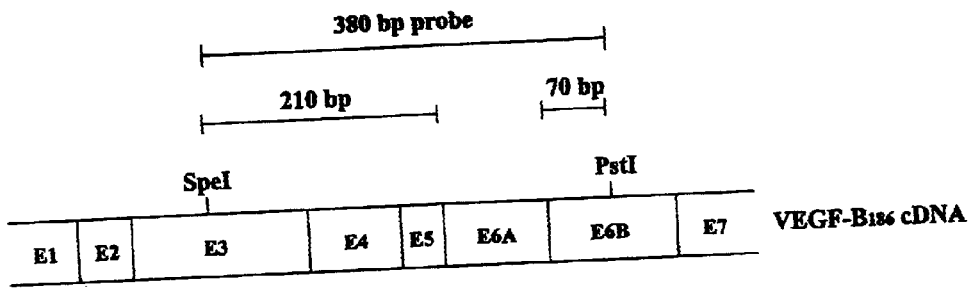
FIG. 1 is a schematic representation of the RNA probe for the two isoforms of mouse VEGF-B used in the RNASE protection analysis.
Figure 2:
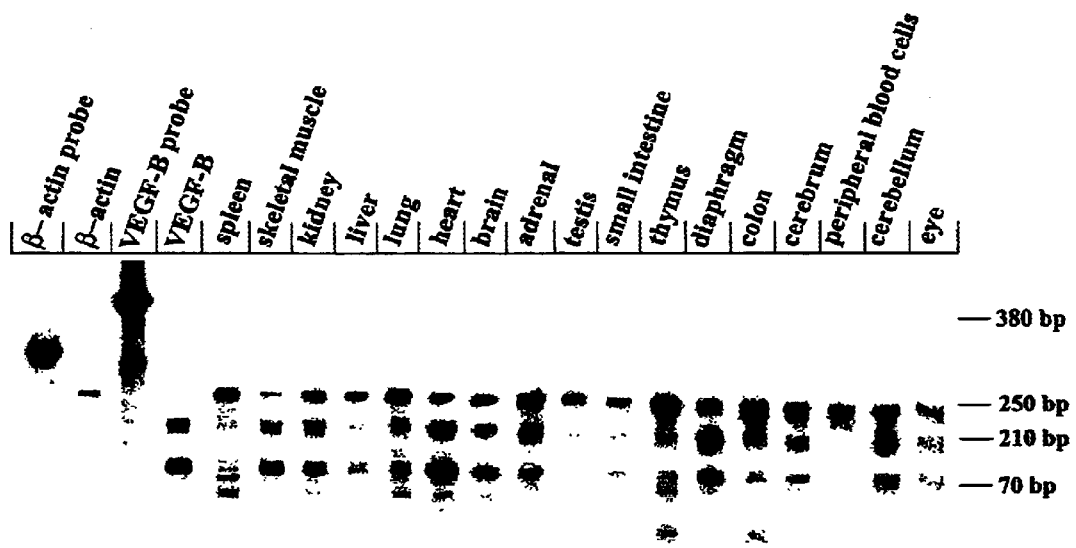
FIG. 2 shows the results of the RNASE protection analysis to determine the distributions and expression levels of the two mouse VEGF-B isoforms using 30 μg of total cellular RNA.

Quantitative RNASE protection analysis was used to determine the distributions and expression levels of the two VEGF-B isoforms. A mouse VEGF-B cDNA fragment of about 380 bp was generated by SpeI and PstI digestion of the mouse VEGF-B gene (MMU52820) covering exons 3, 4, 5, 6A and 6B (See FIG. 1-where the boxes show the respective exons). This fragment was cloned and used as a template to make an RNA probe. Riboprobes were prepared using RNA polymerase (Promega) and $^{32}$P-UTP (Amersham) according to the manufacturers protocol. Using this probe, the VEGF-$B_{167}$ isoform can be distinguished from the VEGF-$B_{186}$ isoform because of the lack of exon 6A. RNASE protection analysis (RPA, Ambion) was used to quantify the expression levels of different genes in different tissues. Briefly, 30 μg of total cellular RNA was hybridized to the riboprobes at 45° C., followed by RNASE digestion. The total cellular RNA was prepared using the guanidinium thiocyanate/acid phenol method as described in Chomczynski and Sacchi, Anal Biochem. 162:156–9 (1987) and stored at −80° C. The digested product was separated on a 6% polyacrylamide gel, and the signals were quantified by phosphor imager. As seen in FIG. 2, RNASE protection analysis showed that when using 30 μg of total cellular RNA, only the VEGF-$B_{167}$ isoform is detectable as indicated by the presence of the 210 and 70 bp fragments, and the absence of the expected 386 bp fragment derived from VEGF-$B_{186}$. This indicates that the VEGF-$B_{167}$ isoform is highly expressed while the VEGF-$B_{186}$ isoform is expressed at very low level, if any. The transcription level of VEGF-$B_{167}$ was quantified by phosphor imager using beta-actin (Ambion) as an internal control.

A table listing the determined expression levels of VEGF-$B_{167}$ from various tissues using 30 μg of total cellular RNA is presented in FIG. 3. The highest expression is seen in heart, skeletal muscle and diaphragm in normal adult mouse tissues, while a lower expression level can be seen in most other tissues. All the values are arbitrary numbers normalized against the internal control, beta-actin.

Figure 4:
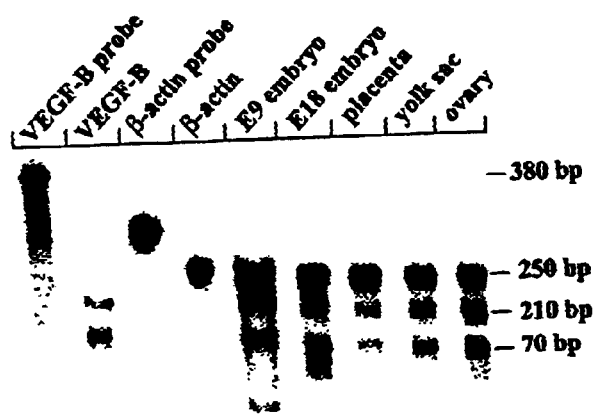
FIG. 4 shows the results of the RNASE protection analysis to determine expression levels of the two mouse VEGF-B isoforms using 30 μg of total cellular RNA extracted from embryos of different developmental stages and other embryonic tissues.

To verify if this expression pattern of VEGF-B is developmental specific, the same experiment was performed using RNA extracted from embryos of different developmental stages and other embryonic tissues. FIG. 4 shows that VEGF-$B_{167}$ isoform is also the predominant transcript in these tissues. VEGF-$B_{167}$ is the major isoform expressed in embryos and other tissues as indicated by the presence of the 210 and 70 bp fragments, and the absence of the 380 bp fragment. 30 μg of total cellular RNA were used in this assay. Both normal adult and embryonic mouse tissues were snap frozen upon collection, and stored at −80° C. until usage.

EXAMPLE 2

VEGF-$B_{186}$ is Expressed at Lower Level in a Tissue-specific Way

Figure 5:
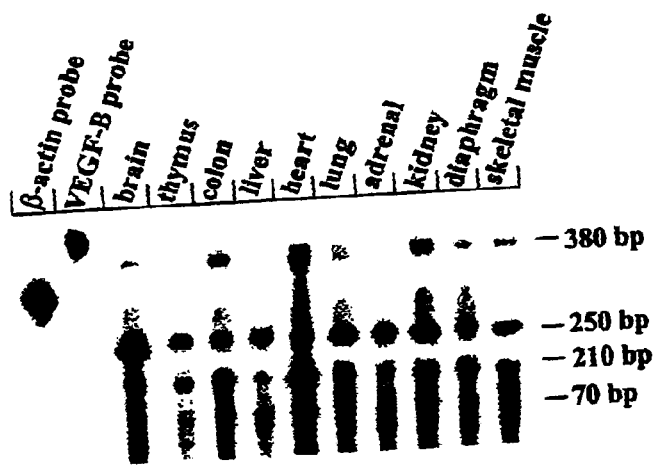
FIG. 5 shows the results of the RNASE protection analysis to determine the distributions and expression levels of the two mouse VEGF-B isoforms using 100 μg of total cellular RNA.

Since VEGF-$B_{186}$ expression was undetectable using 30 μg of total cellular RNA, 100 μg of RNA was used in RPA assay using the same probe and performed in the same way as in Example 1 to investigate the expression of VEGF-$B_{186}$ in adult mouse tissues. FIG. 5 shows that when 100 μg of RNA were used, a fragment of 380 bp derived from VEGF-$B_{186}$ was weakly detectable in some of the tissues tested. The 380 bp fragments were quantified by phosphor imager using beta-actin as an internal control. The results of VEGF-$B_{186}$ expression are also presented in FIG. 3. VEGF-$B_{186}$ is expressed in heart, skeletal muscle, diaphragm, colon, kidney, brain and lung, and is not detectable in the other tissues. It should be noted that the VEGF-$B_{167}$ isoform is expressed in most of the tissues examined, while VEGF-$B_{186}$ is present in limited numbers of tissues. Thus, the VEGF-$B_{186}$ isoform is expressed at low level in adult mouse tissues in a tissue-specific way. These results indicate that there is a different genetic control of the two isoforms of VEGF-B, and possibly, different biological functions. The genetic controls of the two isoforms of VEGF-B is in a tissue-specific way, rather than developmental specific.

To compare the relative expression levels of the two isoforms, a ratio of VEGF-$B_{186}$/VEGF-$B_{167}$ was made by comparing the intensity of the 380 and 210 bp bands. This comparison is presented in FIG. 3. Data show that highest ratios are seen in heart, kidney and colon, which is about 25%. However, taking into consideration the differences in length of the two protected fragments, which is in proportion to the incorporated radioactivity, the expression level of VEGF-$B_{186}$ is about 14% of that of VEGF-$B_{167}$ in the highest expression tissues, and even lower in other organs.

EXAMPLE 3

VEGF-$B_{186}$ is Up-regulated in Mouse Tumor Cell Lines

Figure 6:
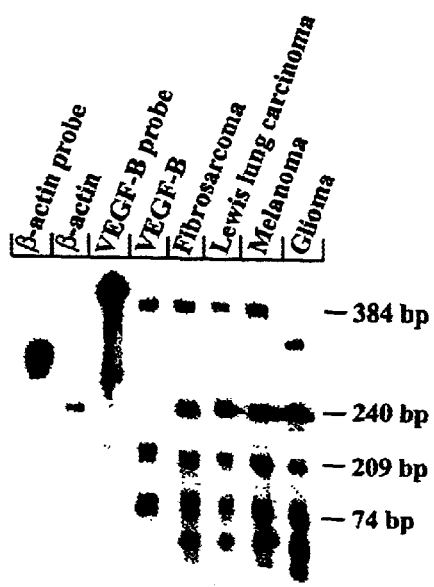
FIG. 6 shows the results of the RNASE protection analysis to determine the expression levels of the two mouse VEGF-B isoforms in mouse tumor cell lines using 30 μg of total cellular RNA.

To investigate the expression pattern of the two isoforms of VEGF-B in tumor cell lines, total cellular RNA (30 μg each) extracted from different mouse tumor cell lines, including fibrosarcoma (T241), melanoma (B16), Lewis lung carcinoma (LLC) and rat glioma (BT4C) were used in this study. The RPA assay was performed in the same way as in Example 1. Surprisingly, the VEGF-$B_{186}$ isoform is highly expressed in all the cell lines tested, indicating an up regulation of the VEGF-$B_{186}$ isoform (see FIG. 6). Beta-actin was used as an internal control for quantification. The relative ratio of VEGF-$B_{186}$/VEGF-$B_{167}$ is greater than 50%, much higher than those observed in normal tissues.

EXAMPLE 4

VEGF-$B_{186}$ is Highly Expressed in Human Melanoma Cell Lines

Figure 7:
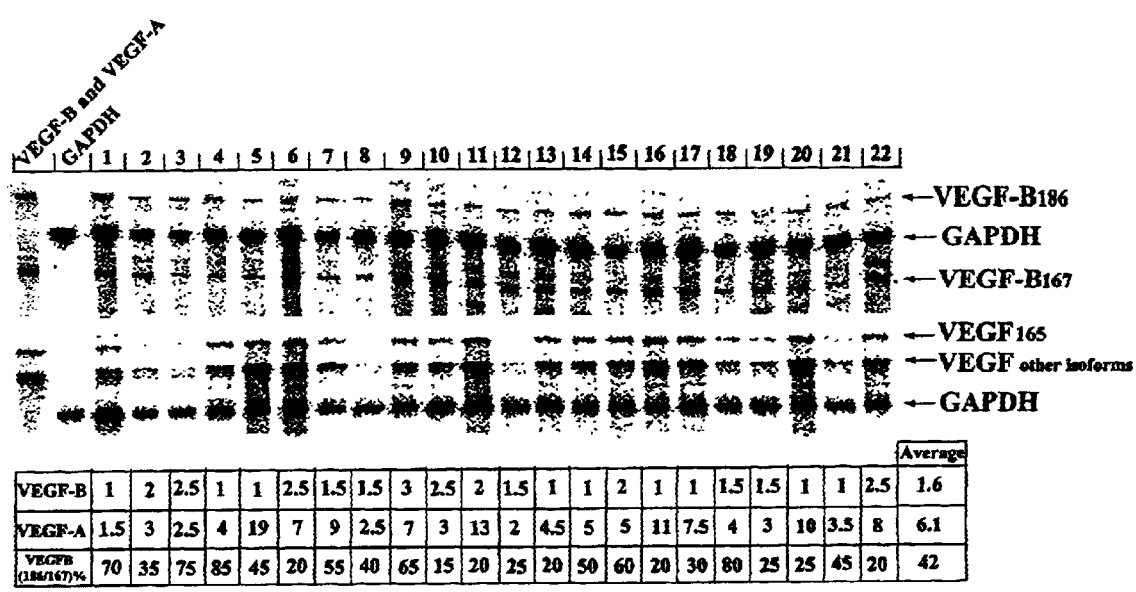
FIG. 7 shows the results of the RNASE protection analysis to determine the expression levels of the two human VEGF-B isoforms in human tumor cell lines using 30 μg of total cellular RNA.
Figure 8:
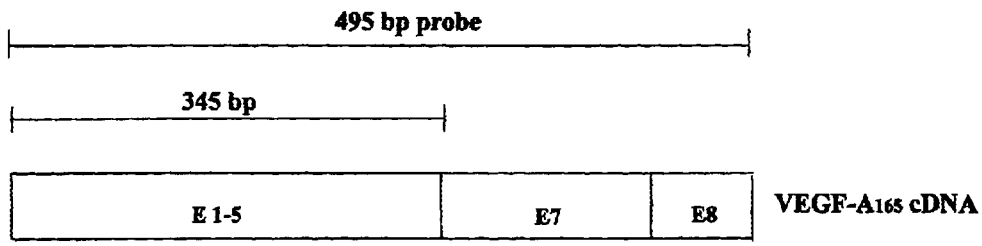
FIG. 8 is a schematic representation of the RNA probe for the isoforms of human VEGF used in the RNASE protection analysis.

To look at the expression of the two isoforms of VEGF-B in human tumor cell lines, a human VEGF-B (U52819) cDNA fragment of about 450 bp was generated by SacI digestion. This fragment was cloned and used as templates to make an RNA probe in the RNASE protection analysis using the same strategy as in Example 1. Twenty-two different human melanoma cell lines were investigated using 30 μg of total cellular RNA. Glyceraldehyde-3-phosphate dehydrogenase (GAPDH) was used as an internal control for quantification. The upper panel of FIG. 7 shows that in most of the cell lines tested, both VEGF-$B_{186}$ and VEGF-$B_{167}$ are highly expressed, displaying an average 186/167 ratio of 42% (see comparison table of FIG. 7). The total VEGF-B expression level was quantified by combining both isoforms and normalizing against the internal control, GAPDH. Both isoforms of VEGF-B are present in all the cell lines, with a higher level in samples 3, 6, 10 and 22. As a comparison, VEGF-A expression was investigated using an about 650 bp cDNA fragment of the human VEGF$_{165}$ isoform (X62568). This fragment was cloned and used as templates to make an RNA probe. As seen in FIG. 8, VEGF-$A_{165}$ isoform is expected to give two protected bands, the fully protected VEGF-$A_{165}$ isoform, and the exons 1–5 region from other isoforms. The boxes in FIG. 8 are the respective exons of VEGF-A. As seen in the lower panel of FIG. 7, VEGF-A is expressed in all the cell lines with dramatic variations of transcription levels, in contrast to that of VEGF-B, which is relatively stable. VEGF-A is highly expressed in samples 5, 7, 11, 16 and 20, where VEGF-B expression levels are under the average value (see comparison table of FIG. 7). This reciprocal expression pattern of VEGF-A and VEGF-B may indicate a potential compensatory role of each other.

EXAMPLE 5

Expression of VEGF-B and VEGF-A in Human Benign and Malignant Pheochromocytoma

Figure 9:
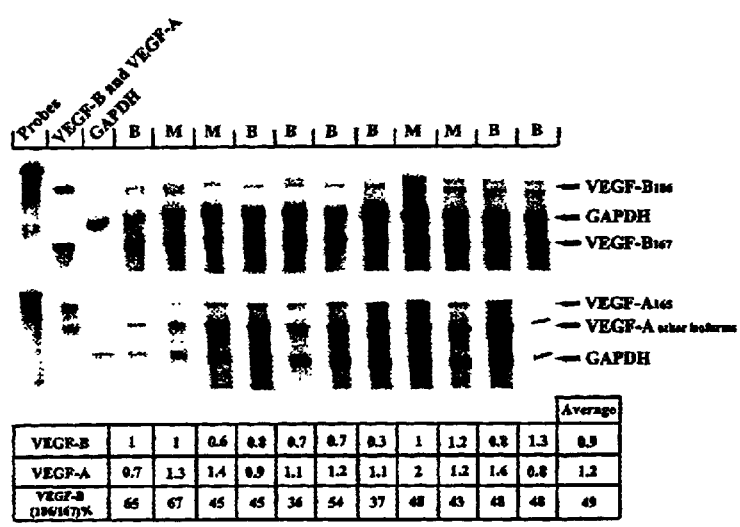
FIG. 9 shows the results of the RNASE protection analysis to determine the expression levels of the two human VEGF-B isoforms and VEGF-A isoforms in human benign and malignant pheochromocytomas.

The isoform specific expression of VEGF-B and VEGF-A were investigated in human benign and malignant pheochromocytomas using the same methods as described in Examples 1 and 4. The upper panel of FIG. 9 shows that VEGF-$B_{186}$ is highly expressed in both benign and malignant tumors, at a similar and high level, with an average VEGF-$B_{186}$/VEGF-$B_{167}$ ratio of about 49% (see comparison table of FIG. 9). The total VEGF-B expression level is similar in benign and malignant samples. This may indicate a prerequisite role of VEGF-$B_{186}$ during malignancy development. The lower panel of FIG. 9 shows that VEGF-A is expressed in both groups at a similar level.

EXAMPLE 6

Both Isoforms of the VEGF-B Protein are Expressed in B16 Melanoma Cells

To verify the protein synthesis of VEGF-B in tumor cells, indirect immunofluorescence microscopy was performed on B16 mouse melanoma cells. B16 mouse melanoma cells were seeded in six-well dishes on sterilized coverslips at a density of 100,000 cells per well one day prior to indirect immunofluorescence microscopy. The localization of VEGF-B was carried out as described in Andersson et al, J Virol., 71:4717–27 (1997). Isoform-specific antibodies directed towards the different C-terminals of VEGF-$B_{167}$ and VEGF-$B_{186}$ were used. The VEGF-$B_{167}$ and VEGF-$B_{186}$ specific antibodies were diluted to a concentration of 20 mg/ml while an endoplasmic reticulum (ER) specific marker Calnexin (Santa Cruz Biotechnology) was used at a dilution of 1:50. The rabbit Ig was visualized with fluorescein isothiocyanate (FITC)-conjugated anti-rabbit IgG antibodies and is seen as a green staining. The goat Ig was visualized with tetramethyl isothiocyanate (TRITC)-conjugated anti-goat IgG antibodies and is seen as a red staining. Immunofluorescence was detected using a Zeiss Axiophot fluorescence microscope.

Figure 10:
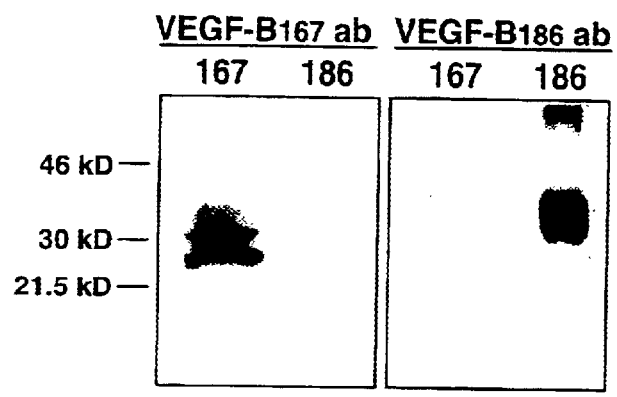
FIG. 10 shows the binding of the VEGF-$B_{167}$ and VEGF-$B_{186}$ specific antibodies with their respective isoform.

VEGF-$B_{167}$ and VEGF-$B_{186}$ specific antibodies were made as follows. PCR fragments of either exon 6B or exon 6A–B encoding the C-terminal for VEGF-$B_{167}$ and VEGF-$B_{186}$, respectively, were generated. For VEGF-$B_{167}$, sense primer 5'ACGTAGATCTAGCCCCAGGATCCTC (SEQ ID NO:1) and antisense primer 5'ACGTGAATTCTCAGC-CCCGCCCTTGGCA (SEQ ID NO:2) were used. For VEGF-$B_{186}$, sense primer 5'ACGTAGATCTAGGGTTGC-CATACCC (SEQ ID NO:3) and antisense primer 5'ACGT-GAATTCTCAGTTGACGGCGCTGGGT (SEQ ID NO:4) were used. The sense primers included a BglII restriction site and the antisense primers an EcoRI site for cloning. The fragments were cloned into the pGEX-2T vector (Pharmacia). GST-fusion proteins were prepared according to the manufacturer's recommendations (Pharmacia). Purified proteins were used to immunize rabbits as described in Aase et al, Dev Dyn., 215:12–25 (1999). VEGF-$B_{167}$ antibodies were affinity purified against the GST-fusion protein and VEGF-$B_{186}$ antibodies against the baculovirus derived protein. The specificity of the affinity purified VEGF-B antibodies were tested by immunoblotting using reduced VEGF-$B_{167}$ and VEGF-$B_{186}$ proteins produced by baculovirus-infected Sf9 cells and separated by 12.5% SDS-PAGE as described in Aase et al, Dev Dyn., 215:12–25 (1999). FIG. 10 shows that the VEGF-$B_{167}$ and VEGF-$B_{186}$ specific antibodies only react with their respective isoform.

Figure 11:
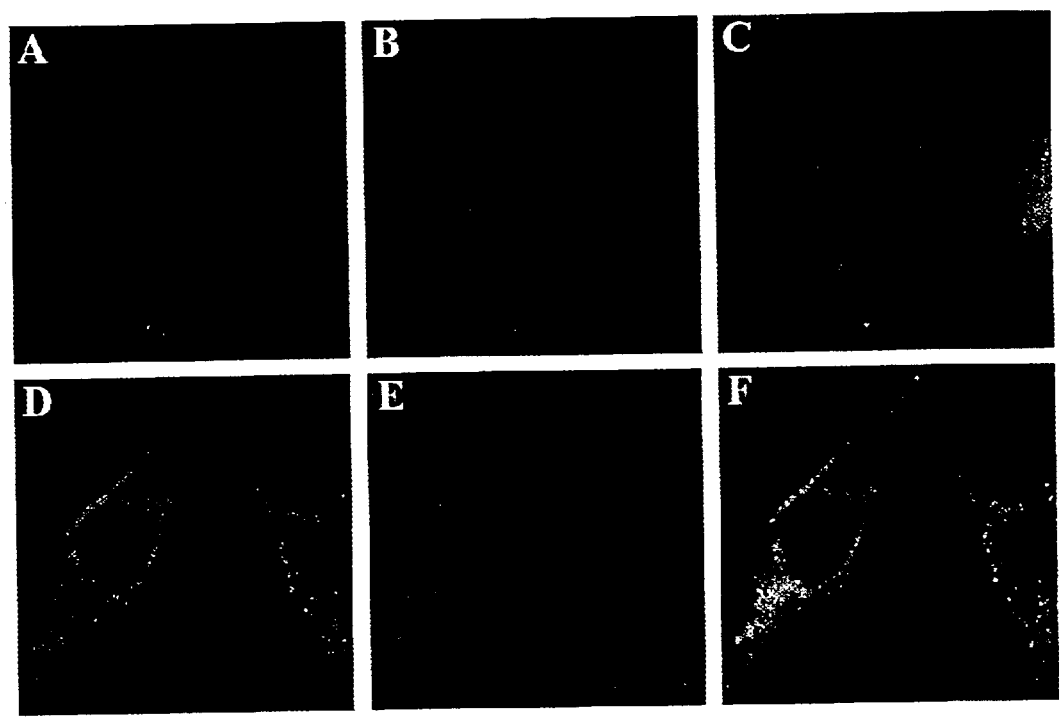
FIGS. 11A–11F show the results of the indirect immunofluorescence microscopy of mVEGF-B and calnexin to verify protein synthesis of VEGF-B in B16 mouse melanoma cells.

FIGS. 11A–11F show the results of the indirect immunofluorescence microscopy of the double immunofluorescence stainings of mVEGF-B and calnexin. FIGS. 11A and 11D show a strong staining of both isoforms in the B16 cells. FIGS. 11B and 11E show the staining of the ER specific marker Calnexin. FIGS. 11C and 11F show the expression of VEGF-B co-localizes with Calnexin. Thus, this indicates that both isoforms of the VEGF-B protein are expressed in B16 melanoma cells.

Taken together these results indicate a maintenance role of VEGF-$B_{167}$ and a potential growth promoting role of VEGF-$B_{186}$ in tumor cell lines, considering the high expression level of VEGF-$B_{167}$ in normal tissues and the up-regulation of the VEGF-$B_{186}$ isoform in tumor cell lines.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for detecting the presence of tumor cells in an animal suspected of having a tumor, comprising the steps of:

obtaining a sample from said animal;

measuring in a $VEGF-B_{186}$-specific manner, the expression level of $VEGF-B_{186}$ in said sample;

determining the control expression level of $VEGF-B_{186}$ in an equivalent sample from an animal not suspected of having a tumor; and comparing said measured expression level with said control expression level, wherein determination of an increased expression of $VEGF-B_{186}$ over the control expression is indicative of the presence of tumor cells.

2. The method of claim 1, wherein said animal is a mammal.

3. The method of claim 1, wherein said animal is a human.

4. The method of claim 1, wherein said animal is a rodent.

5. A method for detecting the presence of tumor cells in an animal suspected of having a tumor, comprising the steps of:

obtaining a sample from said animal;

determining the expression level of $VEGF-B_{186}$ in said sample;

determining the expression level of $VEGF-B_{167}$ in said sample; and comparing said expression level of $VEGF-B_{186}$ with said expression level of $VEGF-B_{167}$, wherein a comparison demonstrating a relative ratio of $VEGF-B_{186}$ to $VEGF-B_{167}$ greater than or equal to 28% is indicative of the presence of tumor cells.

6. The method of claim 5, wherein said animal is a mammal.

7. The method of claim 5, wherein said animal is a human.

8. The method of claim 5, wherein said animal is a rodent.

9. A method for detecting the presence of tumor cells in an animal suspected of having a tumor, comprising the steps of:

obtaining a sample from said animal;

determining the expression level of $VEGF-B_{186}$ in said sample;

determining the expression level of $VEGF-B_{167}$ in said sample; and comparing said expression level of $VEGF-B_{186}$ with said expression level of $VEGF-B_{167}$, wherein a comparison demonstrating a relative ratio of $VEGF-B_{186}$ to $VEGF-B_{167}$ greater than or equal to 50% is indicative of the presence of tumor cells.

10. The method of claim 9, wherein said animal is a mammal.

11. The method of claim 9, wherein said animal is a human.

12. The method of claim 9, wherein said animal is a rodent.

13. A method according to claim 1, wherein the expression level of $VEGF-B_{186}$ is measured at RNA level.

14. A method according to claim 1, wherein the expression level of $VEGF-B_{186}$ is measured at protein level.

15. A method according to claim 14, wherein the expression level of $VEGF-B_{186}$ is measured using a $VEGF1-B_{186}$ specific antibody.

16. A method according to claim 5, wherein the expression level of VEGF-$B_{186}$ is measured at RNA level.

17. A method according to claim 5, wherein the expression level of VEGF-$B_{186}$ is measured at protein level.

18. A method according to claim 17, wherein the expression level of VEGF-$B_{186}$ is measured using a VEGF1-$B_{186}$ specific antibody.

19. A method according to claim 9, wherein the expression level of VEGF-$B_{186}$ is measured at RNA level.

20. A method according to claim 9, wherein the expression level of VEGF-$B_{186}$ is measured at protein level.

21. A method according to claim 20, wherein the expression level of VEGF-$B_{186}$ is measured using a VEGF1-$B_{186}$ specific antibody.

* * * * *